United States Patent [19]

Uekita et al.

[11] Patent Number: 5,071,733
[45] Date of Patent: Dec. 10, 1991

[54] PATTERNED THIN FILM AND PROCESS FOR PREPARING THE SAME

[75] Inventors: Masakazu Uekita; Hiroshi Awaji; Makoto Murata; Satoshi Mizunuma, all of Kobe, Japan

[73] Assignee: Kanegafuchi Kagaku Kogyo Kabushiki Kaisha, Osaka, Japan

[21] Appl. No.: 459,153

[22] Filed: Dec. 29, 1989

Related U.S. Application Data

[60] Division of Ser. No. 248,683, Sep. 23, 1988, Pat. No. 4,943,471, which is a continuation-in-part of Ser. No. 51,350, May 19, 1987, Pat. No. 4,839,219.

[30] Foreign Application Priority Data

| May 20, 1986 | [JP] | Japan | 61-116390 |
| May 20, 1986 | [JP] | Japan | 61-116391 |
| Sep. 25, 1987 | [JP] | Japan | 62-241640 |
| Apr. 28, 1988 | [JP] | Japan | 63-106048 |

[51] Int. Cl.$^5$ .............................................. G03F 7/039
[52] U.S. Cl. .................................. 430/326; 430/330; 430/270
[58] Field of Search ........................ 430/326, 270, 330

[56] References Cited

U.S. PATENT DOCUMENTS

| 3,312,663 | 4/1967 | Sorenson | 260/47 |
| 3,326,851 | 6/1987 | Tocker | 260/47 |
| 3,551,383 | 12/1970 | Fang | 260/47 |
| 3,694,208 | 9/1972 | Ranz et al. | 430/330 |
| 4,022,732 | 5/1977 | Schwarcz | 260/29.6 NR |
| 4,092,442 | 5/1978 | Agnihotri et al. | 430/330 |
| 4,578,328 | 3/1986 | Kray | 430/330 |
| 4,579,809 | 4/1986 | Irving | 430/326 |
| 4,606,998 | 8/1986 | Clodgo et al. | 430/330 |
| 4,740,396 | 4/1988 | Uekita et al. | 427/434.3 |
| 4,751,171 | 6/1988 | Ogawa | 430/326 |
| 4,801,420 | 1/1989 | Uekita | 264/298 |
| 4,822,853 | 4/1989 | Uekita et al. | 528/125 |
| 4,824,766 | 4/1989 | Ogawa | 430/326 |
| 4,839,219 | 6/1989 | Uekita et al. | 428/220 |
| 4,886,734 | 12/1989 | Moore et al. | 430/326 |

FOREIGN PATENT DOCUMENTS

| 47184 | 3/1982 | European Pat. Off. |
| 54-145794 | 11/1979 | Japan |
| 55-3027 | 8/1980 | Japan |

OTHER PUBLICATIONS

Engel et al, "Polymeric Materials Science and Engineering"—Proceedings of the ACS Division of Polymeric Materials, 1986.

(List continued on next page.)

Primary Examiner—Marion E. McCamish
Assistant Examiner—Christopher D. RoDee
Attorney, Agent, or Firm—Armstrong, Nikaido, Marmelstein, Kubovcik & Murray

[57] ABSTRACT

A patterned thin film suitable for use in electric and electronic devices, prepared from a polymer or a mixture of the polymer and other known compounds capable of forming a thin film by LB technique, said polymer having linear recurring units wherein an organic group $R^1$ having at least 2 carbon atoms and a valence of at least 2 is combined alternately with an organic group $R^2$ having at least 2 carbon atoms and a valence of at least 2 through a bivalent group formed by a reaction of an acid group A containing a hetero atom and a basic group B containing a hetero atom, and wherein a hydrocarbon-containing group $R^3$ having 10 to 30 carbon atoms which may contain a substituent group, is linked by covalent or ionic bond to said recurring units, the number of groups $R^3$ being at least 2 per 10 recurring units. The patterned thin film is prepared by building up a layer or layers of the polymer or a mixture of the polymer and a compound capable of forming a film by LB technique onto a substrate according to the LB technique, irradiating patternwise the built-up film with high energy rays, and developing the irradiated film, or by forming the built-up film in the same manner as above on a patterned, removal film formed on a substrate, and removing the patterned film from the substrate, and if desired, by further subjecting the obtained pattern to a reaction to convert the polymer, when it has a structure as a precursor, into a polymer having a 5-membered or 6-membered heterocyclic structure.

2 Claims, 4 Drawing Sheets

OTHER PUBLICATIONS

Vincett et al, Thin Solid Films, 68, 1980, pp. 135–171.
Cemel et al, J. Polym. Sci., Part A-1, vol. 10, 2061–2083 (1972).
Enkelmann et al, J. Poly. Sci.: Poly. Chem Ed., vol. 15, 1843–1854 (1977).
Barraud et al, J. Colloid Interface Sci., vol. 62, 509–523 (1977).
Lieser et al, Thin Solid Films, vol. 68, 77–90 (1980).
Tredgold et al, Thin Solid Films, vol. 99, 81–85 (1983).
Tredgold et al, J. Phys. D: Appl. Phys., vol. 18, 2483–2487 (1985).
"Method for preparation of polyimide monomolecular film and built-up film", a brochure handed out at Fine Chemical Exposition, Mar. 11–13, 1986.
"Polyimide Built-up Film", a preprint for the Annual Spring Meeting of Japan Chemical Society, Apr. 1, 1986.
Engel et al, J. Am. Chem. Soc., 1985, 107, pp. 8308–8310.
Suzuki et al, Chemistry Letters, 1986, pp. 395–398.
Kakimoto et al, Chemistry Letters, 1986, pp. 823–826.

PATTERNED THIN FILM AND PROCESS FOR PREPARING THE SAME

CROSS-REFERENCE TO RELATED APPLICATION

This is a division, of application Ser. No. 248,683 filed Sep. 23, 1988, U.S. Pat. No. 4,943,471. Which is a continuation-in-part of application Ser. No. 051,350 filed on May 19, 1987, and issued as U.S. Pat. No. 4,839,219.

BACKGROUND OF THE INVENTION

The present invention relates to a thin film having a pattern and a process for the preparation thereof. More particularly, the invention relates to a patterned thin film of a high molecular compound modified so as to be able to form a film by Langmuir-Blodgett technique (hereinafter referred to as "LB technique") and a process for preparing a patterned thin film by forming a thin film according to the LB technique and forming a pattern in the film. The patterned thin film is suitable for use in electronic devices, and when the high molecular compound has a precursor structure capable of forming a 5-membered or 6-membered ring, a patterned, heat resistant polymer thin film is obtained.

In the 1930s, it was found by Langmuir and Blodgett that a fatty acid having 16 to 22 carbon atoms could form a monolayer (monomolecular film) on the surface of water and the monolayers could be built up on a substrate to form a multilayer film. In recent years, various studies have been made on the applications of the built-up films, namely Langmuir-Blodgett films (hereinafter referred to as "LB film"). Outline of the studies made hitherto is disclosed in, for instance, Kotai Butsuri 17, No. 12, 45(1982); Thin Solid Films, 68, No. 1 (1980); Thin Solid Films, 99, No. 1.2.3 (1983); Insoluble monolayers at liquid-gas interfaces (G.L. Gains, Interscience Publishers, New York, 1966); and the like.

Conventional LB films of straight-chain saturated fatty acids are poor in heat resistance and mechanical strength and are not suitable for practical uses. In order to improve these defects, it is proposed, for instance, to polymerize films formed from unsaturated fatty acids such as ω-tricosenoic acid, ω-heptadecenoic acid and α-octadecylacrylic acid, unsaturated fatty acid esters such as vinyl stearate and octadecyl acrylate, or diacetylene derivatives. However, these films are insufficient in heat resistance, electric property and other properties. It is also known that some hydrophilic group-containing polymers, such as polyacrylic acids, polyvinyl alcohols, polyethyl acrylates and polypeptides, have film-forming properties. However, none of them are suited as a material for LB films, and no investigations have been made on modification of polymers to make usable, in particular, as a material for LB films.

The present inventors made a study in order to provide LB-films having good heat resistance and mechanical strength, and they have already found and reported in Japanese Unexamined Patent Publication Kokai No. 3024/1988 and EP-A-0230539 that a polymer wherein substituent groups for imparting a hydrophobic property are introduced in the recurring units thereof, is capable of forming a film by the LB technique, and that when the polymer has a precursor structure capable of forming a 5-membered or 6-membered ring, a heat resistant ultrathin film of a polymer having a 5-membered or 6-membered structure is obtained by subjecting the LB films of the precursor polymer to a reaction. The proposed polymer can be used with a known compound capable of forming a thin film by the LB technique, and the mixture can also provide a thin film by the LB technique.

In view of effective utilization of the above proposed thin film in the field of electronics, it is desirable that a pattern is formed so that the film is patternwise present only at a desired portion. However, no many proposals have been made on pattern formation of ultrathin films like LB films. The only technique proposed is a pattern formation wherein a film of the above-mentioned ω-tricosenoic acid or diacetylene is irradiated patternwise with ultraviolet rays or electron beams to polymerize it, thus giving a negative pattern. The patterned films of these materials are, as stated above, insufficient in heat resistance and electric properties and are not suitable for use in electronic devices.

It is an object of the present invention to provide a patterned thin film suitable for use in electronic devices.

A further object of the present invention is to provide a thin film prepared by the LB technique and having a pattern.

A still further object of the present invention is to provide a patterned thin film having excellent properties such as heat resistance, chemical resistance and mechanical properties, and having a thickness as thin as not more than 10,000 Å.

Another object of the present invention is to provide a process for patterning a ultrathin film prepared by the LB technique.

These and other objects of the present invention will become apparent from the description hereinafter.

SUMMARY OF THE INVENTION

It has now been found that when a built-up film prepared by the LB technique from the polymer proposed in Japanese Unexamined Patent Publication Kokai No. 3024/1988 and EP-A-0230539 or a mixture of this polymer and a known compound capable of forming a film by the LB technique is irradiated with high energy rays such as ultraviolet rays, electron beams and X-rays, if necessary, through a mask, there occurs a difference in solubility between the irradiated portion and the nonirradiated portion, thus a pattern can be formed by development. It has also been found that a pattern can be formed by forming a patterned, after-removable film on a substrate, building up a layer or layers of the above proposed polymer or a mixture of the polymer and the LB film-formable compound onto the patterned film on the substrate according to the LB technique, and removing the patterned film from the substrate.

In accordance with the present invention, there is provided a patterned thin film consisting essentially of a polymer having linear recurring units wherein a first organic group $R^1$ having at least 2 carbon atoms and a valence of at least 2 is combined alternately with a second organic group $R^2$ having at least 2 carbon atoms and having a valence of at least 2 through a bivalent group formed by a reaction of an acid group A containing a hetero atom and a basic group B containing a hetero atom, and wherein a hydrocarbon-containing group $R^3$ having 10 to 30 carbon atoms which may contain a substituent group, is linked by covalent bond or ionic bond to said recurring units, the number of groups $R^3$ being at least 2 per 10 recurring units. The patterned thin film is prepared by building up a layer or layers of the above-mentioned polymer or a mixture of the polymer and a compound capable of forming a film by the LB technique onto a substrate according to the LB technique, irradiating patternwise the built-up film with high energy rays such as ultraviolet rays, electron beams and X-rays, and developing the irradiated film, or by forming the built-up film in the same manner as above on a patterned, removal film formed on a substrate, and removing the patterned film from the substrate.

The present invention also provides a patterned, heat resistant thin film consisting essentially of a polymer having linear recurring units wherein a first organic group $R^1$ having at least 2 carbon atoms and a valence of at least 3 is combined alternately with a second organic group $R^2$ having at least 2 carbon atoms and a valence of at least 2 through two bonding groups at least one of which has a 5-membered or 6-membered ring containing a hetero atom. The patterned, heat resistant thin film is prepared by building up on a substrate according to the LB technique a layer or layers of a polymer having a structure as a precursor, namely a polymer having linear recurring units wherein a first organic group $R^1$ having at least 2 carbon atoms and a valence of at least 3 is combined alternately with a second organic group $R^2$ having at least 2 carbon atoms and a valence of at least 2 through a bivalent group formed by a reaction of an acid group A containing a hetero atom and a basic group B containing hetero atom, and wherein a hydrocarbon-containing group $R^3$ having 10 to 30 carbon atoms is linked by covalent bond or ionic bond to said recurring units, the number of groups $R^3$ being at least 2 per 10 recurring units, and said recurring units having a precursor structure capable of forming a 5-membered or 6-membered ring containing a hetero atom, or a layer or layers of the above-mentioned polymer and a compound capable of forming a thin film by the LB technique, irradiating the built-up film patternwise with high energy rays, developing the irradiated film to form a pattern, and subjecting the remaining built-up film to a reaction to form a 5-membered or 6-membered hetrocyclic ring, or by forming the built-up film in the same manner as above on a patterned, removal film formed on a substrate, removing the patterned film from the substrate to leave the built-up film patternwise on the substrate, and subjecting the resulting patterned built-up film to a reaction to form a 5-membered or 6-membered heterocyclic ring.

According to the present invention, a thin film of a polymer modified so as to be able to form a film by the LB technique can be patterned, and a patterned ultra-thin film having excellent heat resistance, chemical resistance and mechanical properties and having a thickness which has been hardly obtainable in general by a conventional process, namely a thickness of not more than 10,000 Å, especially 10 to 1,000 Å.

BRIEF DESCRIPTION OF THE DRAWINGS

The accompanying drawings are schematic illustrations showing instances of utilization of the patterned thin film of the present invention wherein.

DETAILED DESCRIPTION

Figure 1:
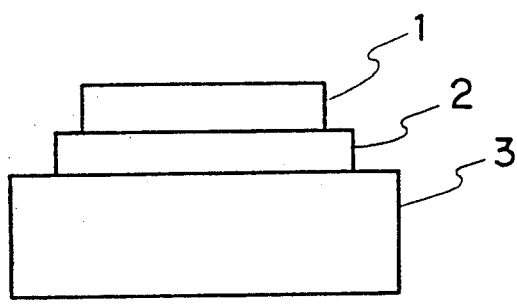
FIGS. 1 to 7 are schematic illustrations of typical devices having a metal/insulation film/semiconductor (MIS) structure.

The high molecular compounds used as a material for forming the LB film in the present invention can be selected from those described in Japanese Unexamined Patent Publication Kokai No. 3024/1988 and EP-A-0230539. In more detail, there are used polymers having linear recurring units wherein a first organic group $R^1$ having at least 2 carbon atoms and a valence of at least 2 is linked alternately with a second organic group $R^2$ having at least 2 carbon atoms and having a valence of at least 2 through a bivalent group formed by a reaction of an acid group A containing a hetero atom and a basic group B containing a hetero atom, and wherein a hydrocarbon-containing group $R^3$ having 10 to 30 carbon atoms which may have a substituent group, is linked by covalent bond to the recurring units to impart a hydrophobic property to the polymers.

The hydrophobic group $R^3$ can be linked by ionic bond to the recurring units. The polymers to which the hydrophobic group $R^3$ is introduced by ionic bond have a structure composed of linear recurring units wherein an organic group $R^1$ having at least 2 carbon atoms and a valence of at least 3 is linked alternately with an organic group $R^2$ having at least 2 carbon atoms and a valence of at least 2 through the bivalent group as mentioned above, and wherein a hydrocarbon-containing group $R^3$ having 10 to 30 carbon atoms which may contain a substituent group, is linked by ionic bond to the recurring units.

The fundamental backbone of the above-mentioned linear recurring units of the polymers is represented by the formula (1), (2) or (3):

  (1)

  (2)

  (3)

In the formulas (1) to (3), each of AB and BA is a bivalent group for bonding the groups $R^1$ and $R^2$, formed by a reaction of an acid group A having a hetero atom such as O, N, S, P or B and a basic group B having a hetero atom such as O, N, S, P or B. The acid group A includes, for instance, —COOR (wherein R is an alkyl group or hydrogen atom, hereinafter the same), —COX (wherein X is Cl or Br, hereinafter the same), —NCO, —NCS, —CN and —CONHR, and the basic group B includes, for instance, —NHR, —OR, ,—SR and —X. Examples of the group AB are, for instance,

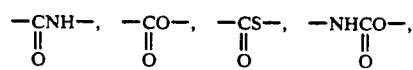

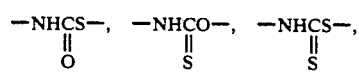

and the like. Examples of the group BA are, for instance,

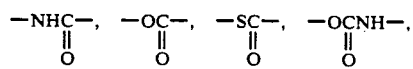

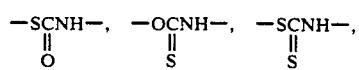

and the like.

When either or both of the groups $R^1$ and $R^2$ are a group characterized by benzenoid unsaturation having at least 6 carbon atoms, not only the obtained thin film has an excellent heat resistance, but also it is considered that the absorption band of the benzenoid structure in ultraviolet region helps that lights in ultraviolet region are efficiently absorbed by the thin film.

Representative examples of each of the group $R^1$ and the group $R^2$ are, for instance,

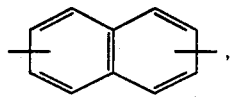

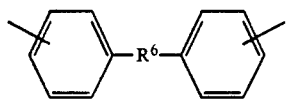

[wherein $R^6$ is $-(CH_2)_{1-3}$, $-\underset{CH_3}{\overset{CH_3}{C}}-$, $-\underset{CF_3}{\overset{CF_3}{C}}-$, $-O-$, $-CO-$, $-S-$, $-SO_2-$, $-\underset{R^7}{\overset{R^7}{N}}-$, $-\underset{R^7}{\overset{R^7}{Si}}-$, $-\underset{R^7}{\overset{R^7}{O-Si-O}}-$, $-\underset{\overset{\|}{O}}{O-P-O}-$ or $-\underset{\overset{\|}{O}}{P}-$ in which $R^7$ is an alkyl or aryl group],

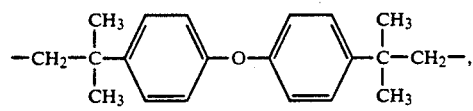

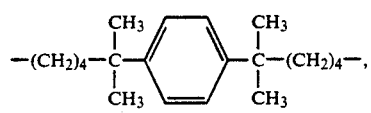

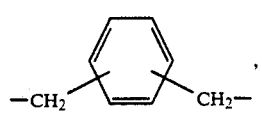

-continued

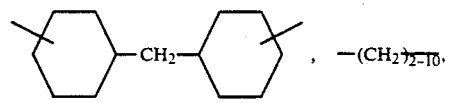

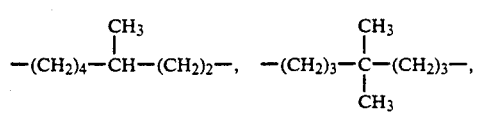

$-(CH_2)-\underset{\underset{CH_3}{|}}{\overset{\overset{CH_3}{|}}{C}}-(CH_2)_3-$, $-(CH_2)_{10}-CH(CH_3)$, $-(CH_2)_3-\overset{\overset{OCH_3}{|}}{CH}-(CH_2)_2-$, $-(CH_2)_3-O-(CH_2)_2-O-(CH_2)_3-$,

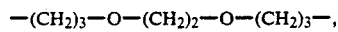

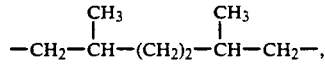

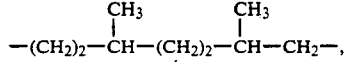

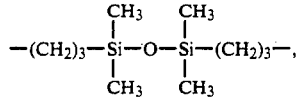

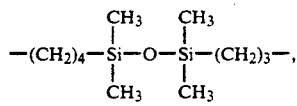

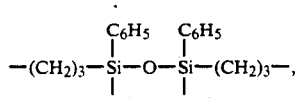

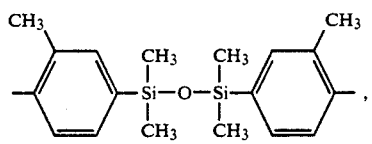

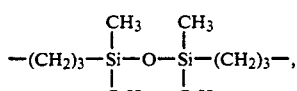

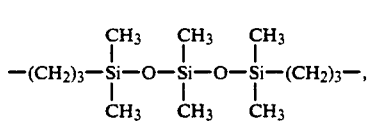

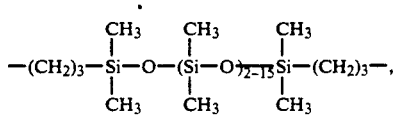

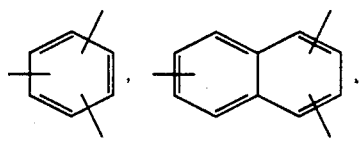

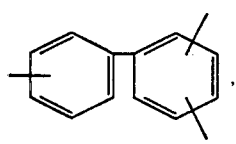

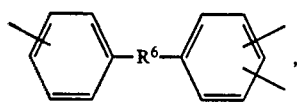

[wherein R⁶ is as defined above]

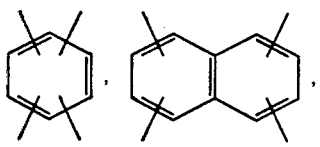

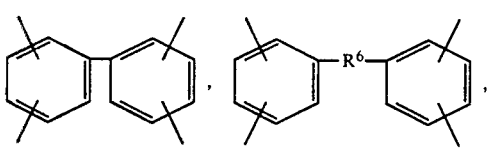

[wherein R⁶ is as defined above]

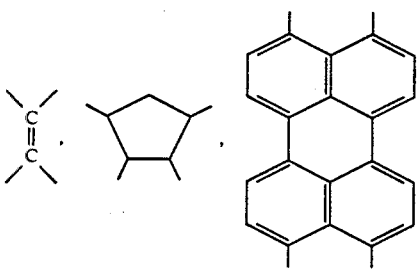

Preferable groups R¹ and R² are as follows:

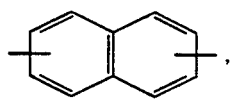

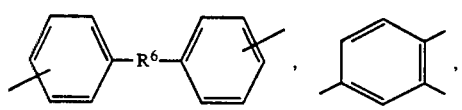

[wherein R⁶ is as defined above]

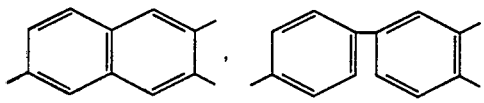

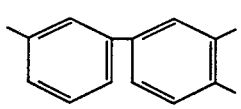

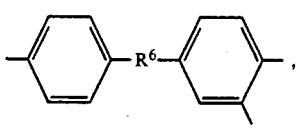

[wherein R⁶ is as defined above]

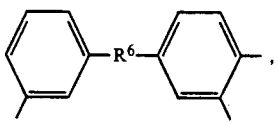

[wherein R⁶ is as defined above]

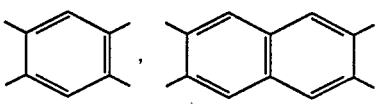

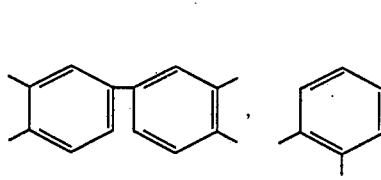

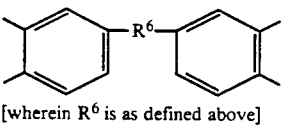

[wherein R⁶ is as defined above]

The number of hydrocarbon-containing groups R³ introduced to impart a hydrophobic property to the polymers, thereby enabling the film formation by LB technique, is at least 2 per 10 recurring units, preferably at least one per recurring unit, more preferably at least 2 per recurring unit.

The hydrophobic group R³ can be attached to any of group R¹, group R² and bivalent group AB or BA in the recurring unit. The group R³ is introduced into the linear recurring units, for instance, by the following three methods:

[I] A method in which the group R³ is substituted for an atom of the group AB or BA in the linear recurring units of the formula (1), (2) or (3);

[II] A method in which the group R¹ or R² is directly substituted by the group R³;

[III] A method in which the group R³ is substituted for an atom of the substituent group of the group R¹ and/or R² at least one of which has a valence of at least 3, the substituent group being one not used for bonding to form the linear recurring units.

The polymers having a precursor structure capable of forming a 5-membered or 6-membered ring are preferred, since they can be converted into a heat resisting structure having a 5-membered or 6-membered ring.

Representative examples of the polymers to which hydrophobic groups R³ have been introduced by covalent bond are, for instance,

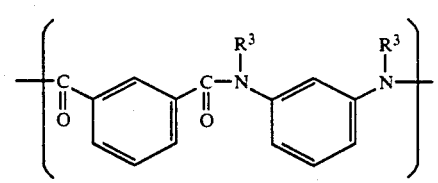
(1)
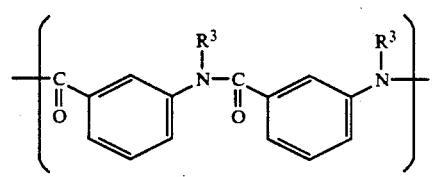
(2)
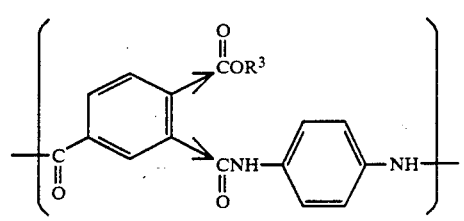
(3)
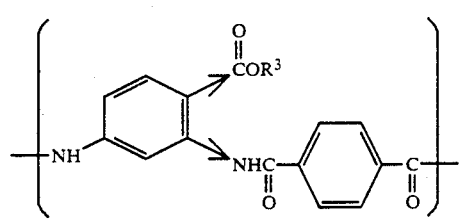
(4)
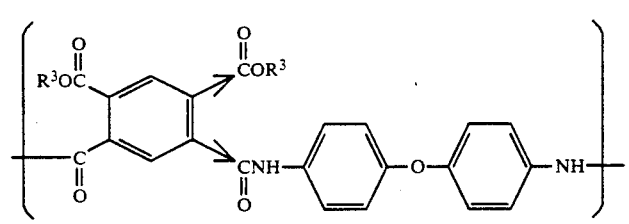
(5)
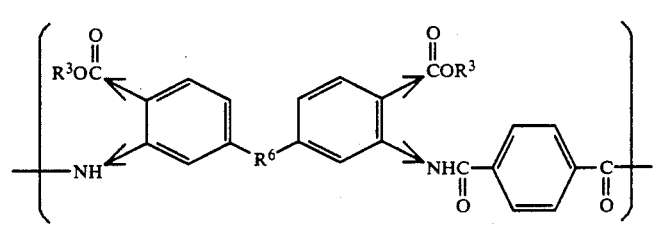
(6)
[wherein $R^6$ is as defined above]
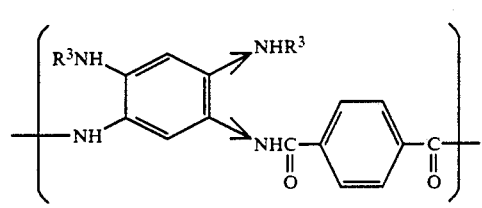
(7)

-continued
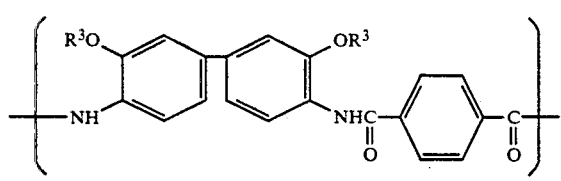
(8)
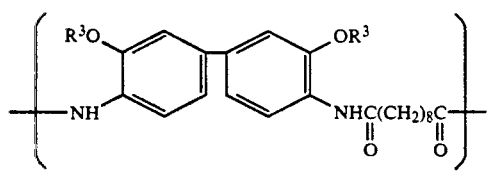
(9)
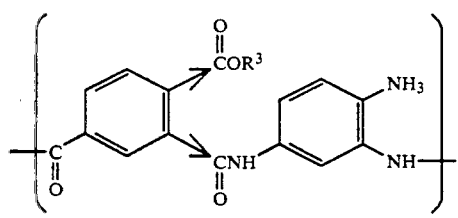
(10)
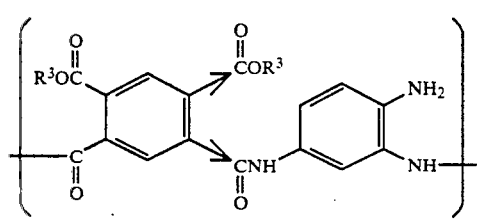
(11)
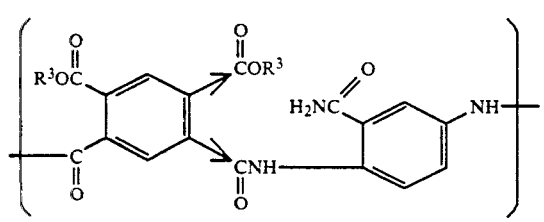
(12)
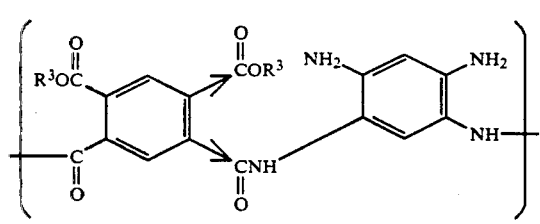
(13)
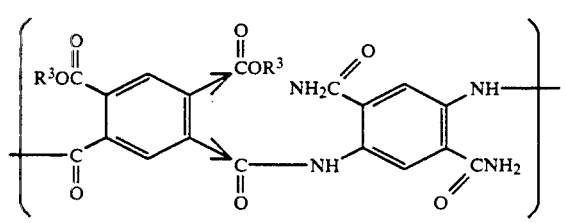
(14)

-continued

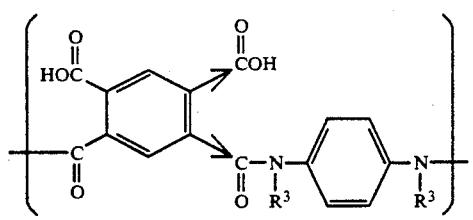 (15)

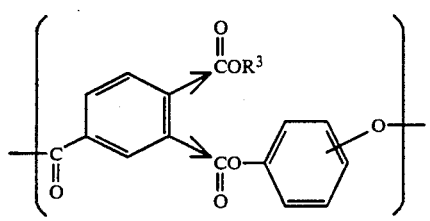 (16)

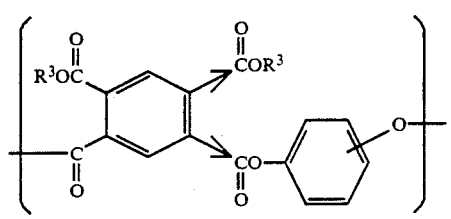 (17)

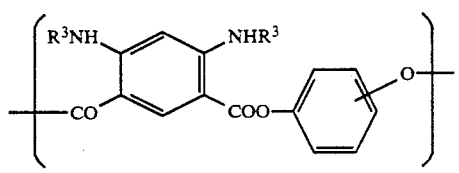 (18)

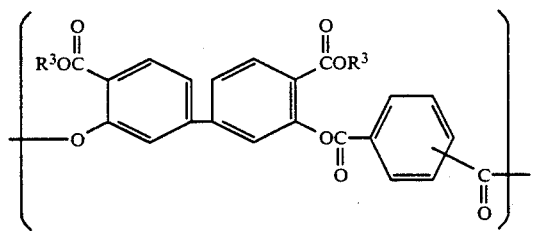 (19)

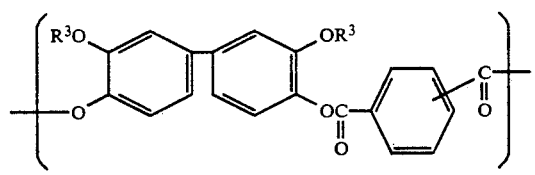 (20)

In the formulas (1) to (20), the group $R^3$ is a hydrocarbon-containing group having 10 to 30 carbon atoms, preferably 16 to 22 carbon atoms. Preferably, the group $R^3$ is a monovalent group selected from an aliphatic group, a group wherein an alicyclic group is combined with an aliphatic group, a group wherein an aromatic group is combined with an aliphatic group, or their substituted groups. Representative examples of the group $R^3$ are, for instance, $CH_3\text{-}(CH_2)_{n-1}$,

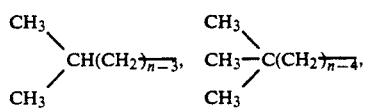

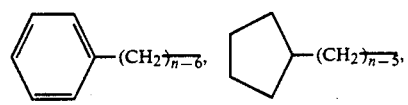

-continued

wherein n is an integer of 10 to 30, preferably from 16 to 22. Among them, a straight-chain aliphatic hydrocarbon group is particularly preferable.

The group $R^3$ may have a substituent. Examples of the substituent are, for instance, a halogen atom, nitro group, amino group, cyano group, methoxy group, acetoxy group, and the like. When occasion demands, group $R^3$ substituted by fluorine is preferred, because fluorine atom rises the hydrophobic property more than hydrogen atom. That is to say, the length of alkyl chain in the group $R^3$ can be shortened by including fluorine atom in the group $R^3$. For instance, in case of $C_8F_{17}(CH_2)_k$—, it is sufficient that k is 2, namely the group $R^3$ having 10 carbon atoms is sufficient for making possible the film formation by the LB technique.

The molecular weight of the polymer used in the present invention is not particularly limited. However, when the molecular weight is too low, films can be formed by the LB technique, but films having good heat resistance, chemical resistance and mechanical strength cannot be obtained. Also, when the molecular weight is too high, the film formation is difficult due to high viscosity. Accordingly, usually the molecular weight of the polymer is selected from about 2,000 to about 300,000, especially about 10,000 to about 150,000.

Representative examples of the polymers to which hydrophobic groups have been introduced by ionic bond are, for instance,

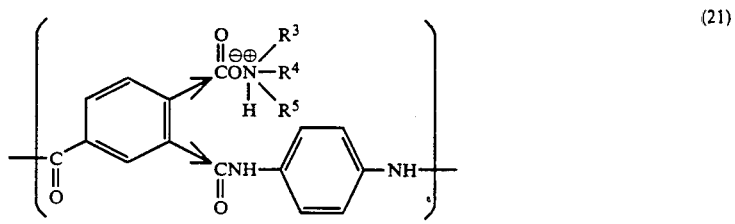
(21)

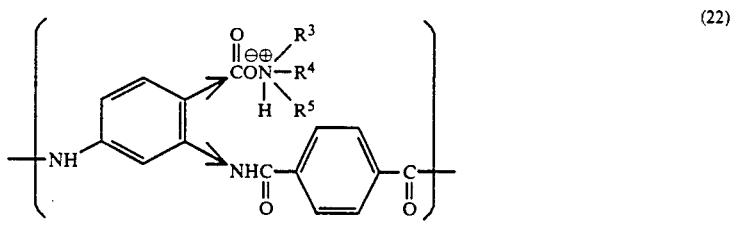
(22)

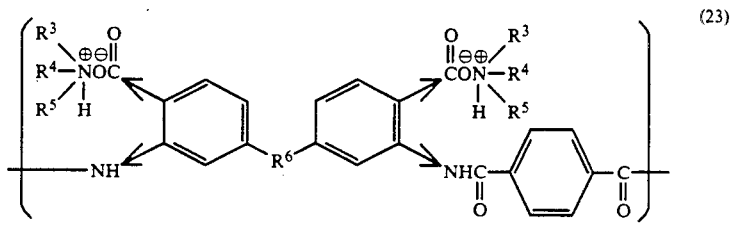
(23)

[In the formula (23), $R^6$ is as defined above.]

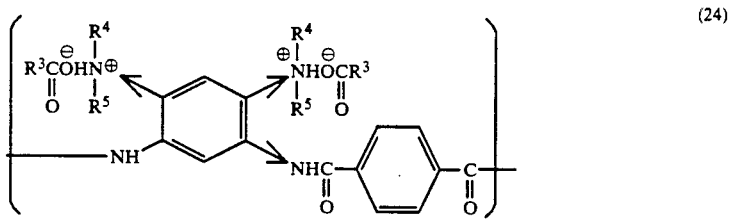
(24)

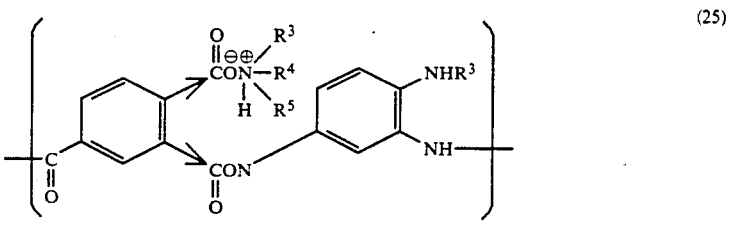
(25)

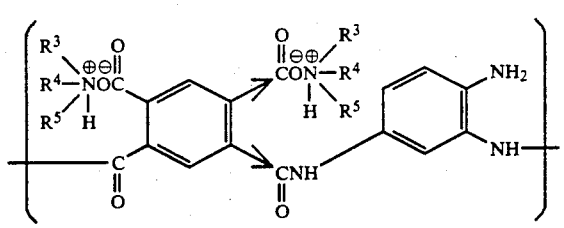
(26)
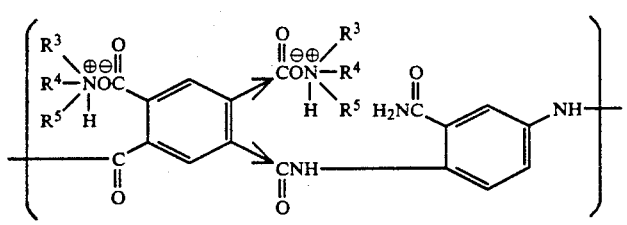
(27)
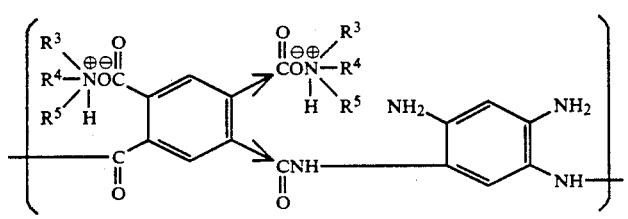
(28)
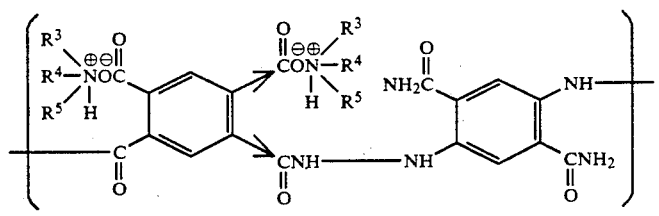
(29)
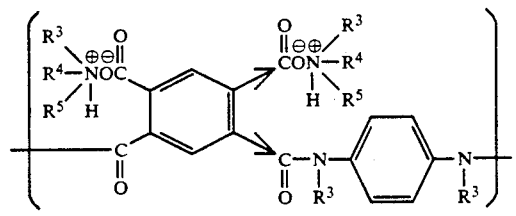
(30)
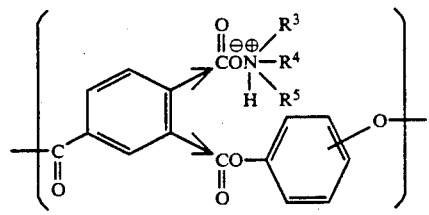
(31)
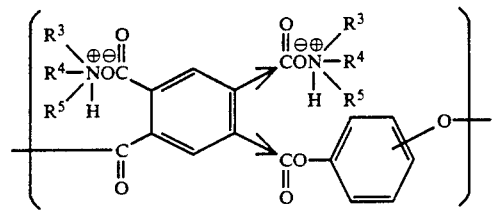
(32)

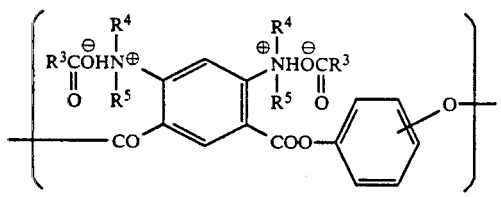

(33)

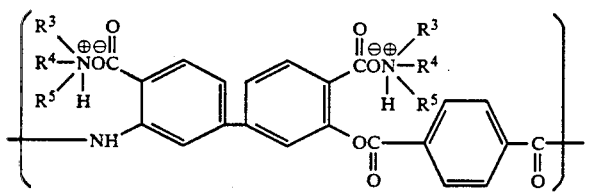

(34)

In the above formulas (3) to (34), the symbol "→" means isomerism. Explaining the isomerism with reference to the recurring unit of the formula (3):

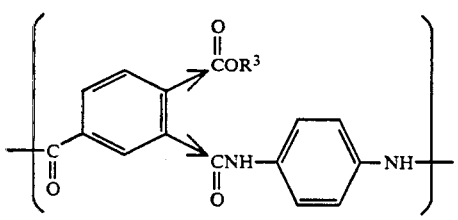

(3)

the above formula represents both the recurring unit of the formula (3-1):

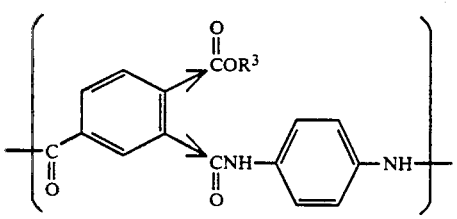

(3-1)

and the recurring unit of the formula (3-2):

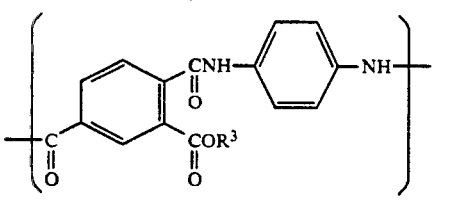

(3-2)

and in such a case, the symbol "→" indicating the isomerism is used.

In the present specification, the term "isomerism" or the symbol "→" comprehends the both cases, one being the case where either one of the recurring units as shown by the formulas (3-1) and (3-2) is present alone, and the other being the case where the recurring units as shown by the formulas (3-1) and (3-2) are present together.

In the polymers as shown by the formulas (21) to (34), at least 2 hydrophobic groups $R^3$ having 10 to 30 carbon atoms are present per 10 recurring units. Preferably at least one hydrophobic group $R^3$, more preferably at least 2 hydrophobic groups $R^3$, are present per recurring unit. In the above formulas (21) to (34), at least one of $R^3$, $R^4$ and $R^5$ is the hydrophobic group, namely hydrocarbon-containing group having 10 to 30 carbon atoms which may have a substituent group. The remainder is a hydrocarbon-containing group having 1 to 30 carbon atoms or hydrogen atom, preferably a hydrocarbon-containing group having 1 to 4 carbon atoms or hydrogen atom.

The polymers usable in the present invention are of course not limited to the above exemplified polymers. Copolymers which are considered from the above exemplified polymers, and mixtures of the above exemplified polymers can also be used.

LB films can be formed from the polymers explained above by any of the so-called LB technique without restriction, e.g. the vertical dipping method (LB method), the horizontal dipping method, the revolving cylindrical method and so on (as described in Shin Jikken Kagaku Koza, Vol. 18, "Interface and Colloid", pages 498-508). The LB technique is a method in which a LB material is spread onto the surface of water and compressed at a constant surface pressure to form monomolecular layer film and the monomolecular layer is transferred onto a substrate.

According to the LB technique, oriented films can be obtained, and moreover the thickness of the films can be controlled in several tens angstroms. Accordingly, the LB technique is advantageous in providing thin films having a thickness of not more than 200 Å or not more than 1000 Å, e.g. several hundreds angstroms or several tens angstroms. Of course, films having a thickness of 10,000 Å or more can be obtained according to the LB technique. The thin films of the invention have such a feature in thickness.

The modified polymers as explained above are able to form thin films by the LB technique. The thin film can be formed from the above modified polymer alone. When the modified polymer is used in combination with a known compound capable of forming films by the LB technique (hereinafter referred to as "LB compound"), the film forming properties can be improved The use of such a mixture as a LB film-forming material is one of preferable embodiments of the invention. In particular, in the case where the hydrocarbon-containing group $R^3$ having 10 to 30 carbon atoms is introduced in a small amount to the recurring units, such a modified polymer is preferably used in combination with the known LB compound. The term "known LB compound" as used herein means compounds known in the art to form films by the LB technique, and they are described, for instance, in the literatures referred to above. Especially, compounds composed of a hydrocarbon group having about 16 to about 22 carbon atoms and a hydrophilic group are preferred as the LB compound to be admixed with the polymer, e.g. $CH_3(CH_2)_{m-1}Z$, $CH_2=CH(CH_2)_{m-2}Z$ and $CH_3(CH_2)_qC\equiv C-C\equiv C(CH_2)_pZ$ wherein Z is OH, $NH_2$, COOH, $CONH_2$ or COOR' in which R' is a lower aliphatic hydrocarbon group, m is an integer of 16 to 22, and $q+p=m-5$. The compound having the formula: $CH_3(CH_2)_{m-1}Z$ wherein Z and m are as defined above is superior in improving the film forming properties and from the viewpoint of the cost. The compound having unsaturated bond has a feature that it can be polymerized by irradiating lights or radiation such as ultraviolet rays or electron beams. The mixing ratio of the modified polymer to the known LB compound is not particularly limited. Usually, the ratio of the modified polymer to the known LB compound is from 0.2 to 2.

In general, a solvent such as benzene or chloroform which evaporates into a gas phase without dissolving in water, is used for spreading an LB film forming material onto the water surface. In case of the modified polymer, it is preferable to use such a usual solvent in combination with an organic polar solvent for increasing the solubility. Examples of the organic polar solvent are, for instance, N,N-dimethylformamide, N,N-dimethylacetamide, N,N-diethylformamide, N,N-diethylacetamide, N,N-dimethylmethoxyacetamide, dimethylsulfoxide, N-methyl-2-pyrrolidone, pyridine, dimethylsulfone, hexamethylphosphoramide, tetramethylenesulfone, dimethyltetramethylenesulfone, and the like.

When the mixture of the polymer and the known LB compound is spread onto the water surface, it is also preferable to use the solvent such as benzene or chloroform in combination with the organic polar solvent.

In case of using the solvent such as benzene or chloroform in combination with the organic polar solvent, it is considered that when a solution for forming LB films is spread onto the water surface, benzene, chloroform or the like evaporates into the gas phase and the organic polar solvent dissolves into a large quantity of water.

The substrates used for forming LB films thereon are not particularly limited, and are selected according to the uses of the formed LB film. Examples of the substrate are, for instance, an inorganic substrate such as glass, alumina or quartz, a metal substrate, a plastic substrate, a substrate of a semiconductor of Groups IV, III-V, II-VI of the Periodic Table such as Si, GaAs or ZnS, a substrate of a ferroelectric substance such as $PbTiO_3$, $BaTiO_3$, $LiNbO_3$ or $LiTaO_3$, a substrate of a magnetic substance, and the like. The substrates may be surface-treated in a usual manner. Surface treatment with a silane coupling agent, especially a silane coupling agent having amino group or epoxy group, or with an aluminum chelate compound, followed by heat treatment improves the adhesion between the thin film and the substrate.

Pattern formation of the LB film is carried out either by irradiating the film patternwise with high energy rays such as X-rays, for instance, irradiating the rays through a mask, and dissolving the exposed area with a developer to leave the unexposed area as a pattern, or by forming a film removable later on a substrate, patterning the removal film, depositing a layer or layers of the polymer or a mixture of the polymer and a known LB compound onto the patterned film on the substrate according to the LB technique, and removing the intermediate patterned film from the substrate, thereby leaving the LB film patternwise on the substrate.

Pattern formation by radiation will be explained in detail below.

A thin film according to the invention is first formed on a substrate by depositing monolayer or monolayers on the substrate according to the LB technique. High energy rays such as ultraviolet rays, electron beams or X-rays are irradiated to the LB film, if necessary, through a mask. Ultraviolet rays are particularly preferable. Also, use of excimer laser light such as KrF is preferable, because a pattern of high resolution can be obtained and because the exposure time can be shortened.

After the exposure, the exposed area is dissolved by a developer to give a pattern.

Although the reason why a pattern is formed by the irradiation method is not made clear, it is considered that the polymer is degraded by severance of main chain, and it appears that it concerns the fact that the polymer has the maximum absorption at $\lambda_{max}$=about 200 nm and about 250 nm.

There are cases where the use of a sensitizer as disclosed in J. Kosar, Light Sensitive Systems (John Wiley & Sons, Inc., New York, 1965, pages 143-146 and 160-188) is preferred, e.g. Michler's ketone, benzoyl ether, 2-t-butyl-9,10-anthraquinone, 1,2-benzo-9,10-anthraquinone, and 4,4'-bis(diethylamino)benzophenone.

As the developer used in the development of patternwise exposed films, there are used mixed solvents of an organic polar solvent such as dimethylacetamide, dimethylformamide, dimethylsulfoxide, hexamethylformamide or N-methylpyrrolidone, and an alcohol such as methanol or ethanol. Aqueous ammonia, an aqueous solution of an alkali and an organic alkaline solution such as tetramethylammonium hydroxide are also suitably used as well as the alcohol.

The pattern formation using a patterned removal film, which is carried out by the following roughly classified two methods, will be explained.

In the first method, a pattern of a photoresist is formed on a substrate. Any photoresist materials can be used in the present invention without restriction, so long as the formed photoresist films can be lifted off under a condition not dissolving the polymer of the invention. The photoresist may be positive type and negative type.

The photoresist is patterned in a usual manner, and a patterned photoresist can be formed from a commercially available photoresist material according to the recommended method therefor. In general, a resist pattern is formed on a substrate by rinsing the substrate, applying a resist material, pre-baking, exposing to lights, developing the exposed resist film, and rinsing and post-baking the patterned resist.

Polymer films are then built up according to the LB technique onto the substrate having the thus formed resist pattern. The built-up film may be dried or partly cured by slight heating. Thereafter, the resist is lifted off from the substrate with a resist releasing agent selected not so as to substantially dissolve the polymer of the invention, thus forming a pattern of the polymer thin film. Examples of the releasing agent are, for instance, acetone, high boiling ketones, methanol, and ethanol.

In the second method, a pattern of a masking tape is first formed on a substrate. Any masking tapes can be used without particular restriction, so long as they are not affected by and have no effect on the film building up operation according to the LB technique. From such a point of view, masking tapes which do not elute a compound having a surface activity into water and which have no water-absorptivity, are preferably used. Polymer films are built up onto the patterned masking tape provided on the substrate according to the LB technique, and then the masking tape is removed from the substrate, for instance, by peeling, thus leaving a patterned LB film on the substrate.

In the case that the polymer used for the LB film formation has a precursor structure capable of forming a 5-membered or 6-membered ring, a heat resistant pattern of the polymer thin film can be obtained by subjecting the patterned thin film to a reaction to convert the polymer to a polymer having a 5-membered or 6-membered ring. It is possible to realize a heat resistance of not lower than 300° C., especially not lower than 500° C., by selecting the molecular structure of the polymer.

For instance, the polymers shown by the formulas (3) to (15) and (21) to (30) have such a structure as being able to be partially or completely ring-closed into a 5-membered or 6-membered heterocyclic ring. After complete ring closure, these polymers have the following structures.

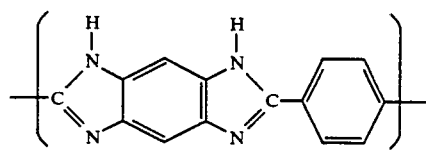
(7')

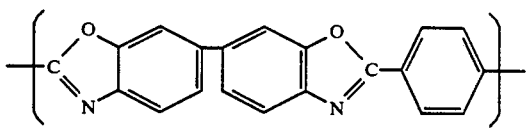
(8')

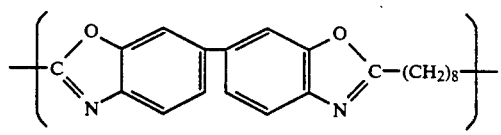
(9')

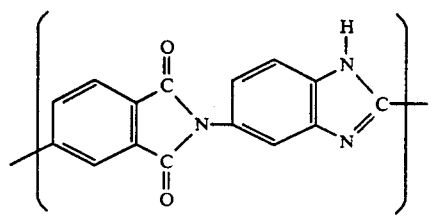
(10')

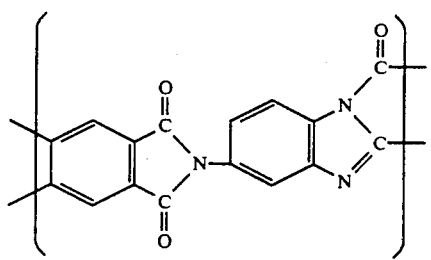
(11')

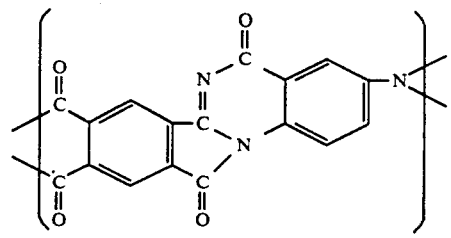
(12')

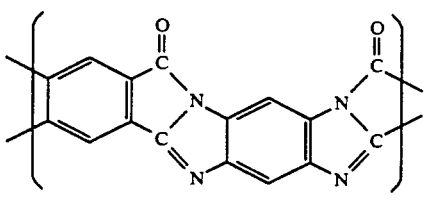
(13')

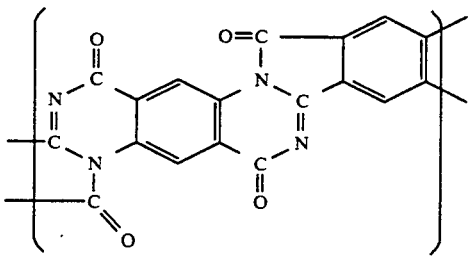
(14')

(3')
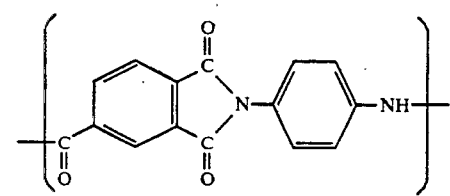

(4')
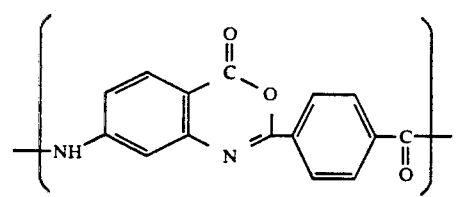

(5')
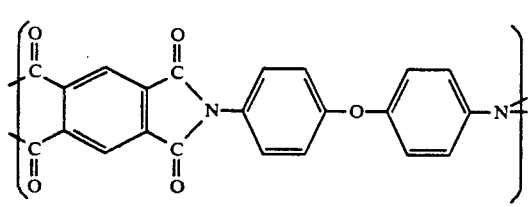

(6')
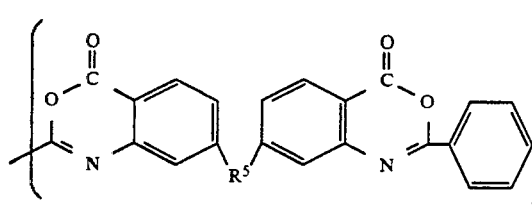

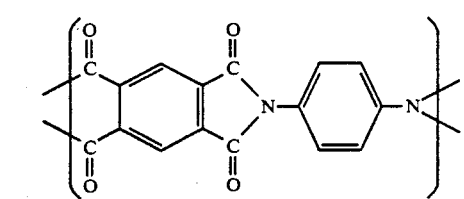
(15')
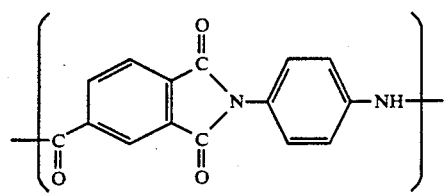
(21')
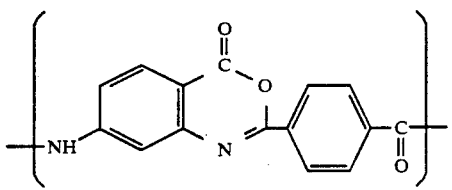
(22')
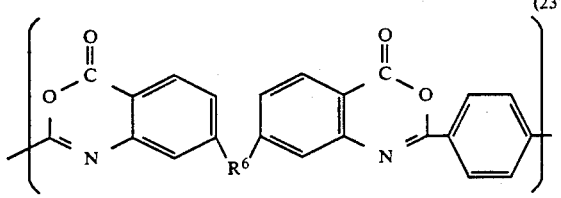
(23')
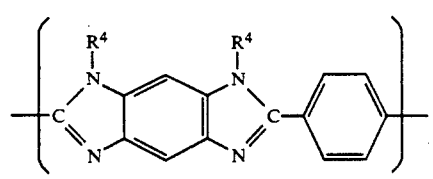
(24')
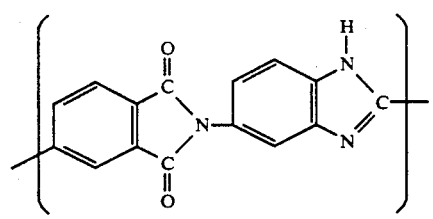
(25')
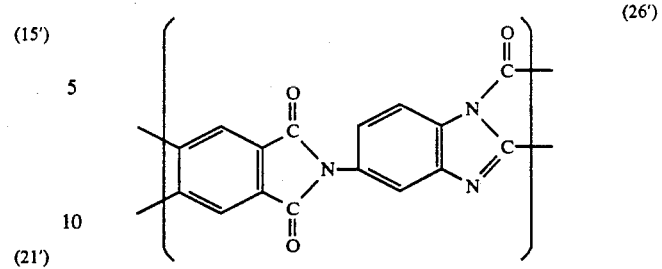
(26')
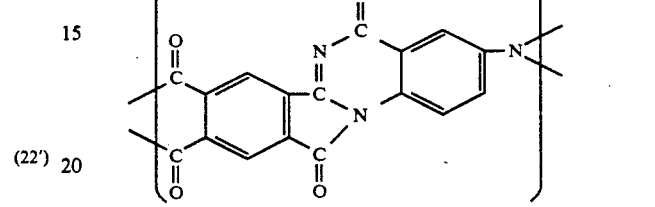
(27')
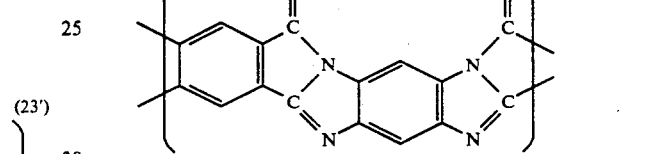
(28')
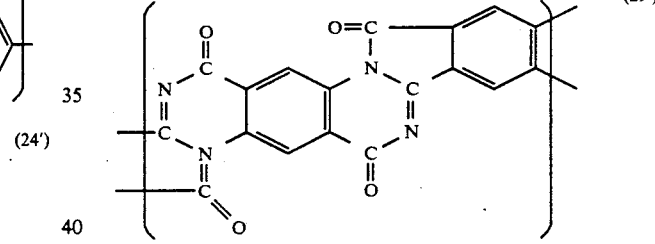
(29')
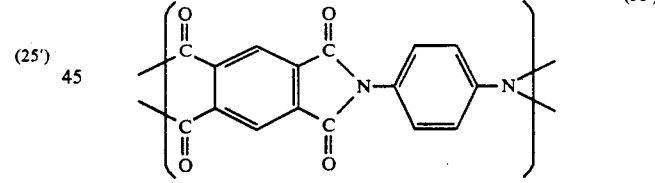
(30')
Methods for the ring closure are not particularly limited. For instance, in case of imidization as represented by the polymer of the formula (5), the ring closure is achieved to produce a polyimide by heating at a temperature of about 300° C. to about 400° C., as shown by the following reaction scheme.
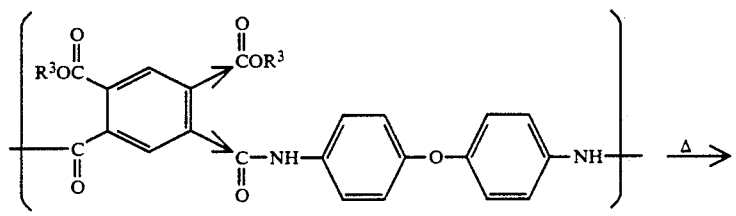

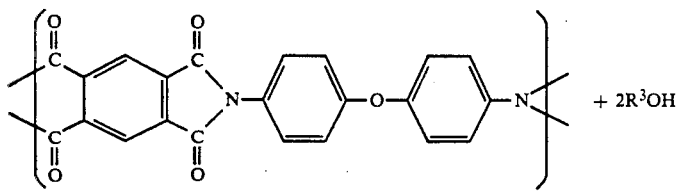

When the polymer converts into polyimide, the groups $R^3$ introduced for imparting a hydrophobic property to a polyamide acid eliminate as an alcohol. Since the eliminated alcohol can be removed away or scattered away, for instance, by conducting the conversion into polyimide in a gas stream or under vacuum at a temperature of about 200° to about 400° C., polyimide films having excellent heat resistance and electric insulation property can be obtained.

In case of obtaining thin films having an excellent heat resistance by conducting the ring-closure reaction, it is preferable that the known LB compounds, when desired to use with the polymer, are selected those able to be removed or scattered away under the ring closure reaction condition.

For imidization, chemical curing agents such as acetic anhydride, pyridine and isoquinoline which have been conventionally used in imidization may of course be used in the invention. Also, such means may be used in combination with thermal means.

When heat-resistant patterned thin films are desired, it is preferable to use polymers wherein the groups $R^3$ are linked to the recurring units by covalent bond, since thin films having a particularly excellent heat resistance are obtained by conducting the ring closing reaction under heating.

The thin films of the present invention obtained by forming a built-up film on a substrate according to the LB technique, patterning the film, and then, if necessary, conducting the ring-closure reaction, have excellent heat resistance, mechanical strength, chemical resistance and electric insulation properties Moreover, they are very thin, that is, they have a thickness of not more than 10,000 Å, e.g. 5000 Å and 2000 Å. If desired, it is possible to obtain thin films having a thickness of 10 to 1000 Å.

In particular, according to the present invention, it is possible to provide thin films having excellent properties, especially a high dielectric strength of not less than $1 \times 10^6$ V/cm, even if the film thickness is less than 1000 Å, for examples, several hundreds of angstroms, or 50 to 100 Å. When selecting polymers having certain molecular structures, thin films having a heat resistance of not less than 300° C., especially not less than 400° C., more especially not less than 500° C., can be obtained. For instance, precursors wherein $R^1$ has a valence of at least 3, having a structure capable of forming a 5-membered or 6-membered hetero ring can provide polymers having excellent heat resistance, e.g. polyamide-imide, polyimide-isoindroquinazolinedione, polyimidazopyrolone and polyoxadinone, and thin films of these heat resistant polymers have an excellent heat resistance as well as an excellent electric insulation property. Therefore, the thin films of the invention can be used in various devices such as electric or electronic devices. In case of thin films having a thickness of about 50 Å to several hundreds angstroms, unique effects produced by the film thickness, e.g. tunnel effect, are expected, and many attractive applications utilizing them become possible.

Next, applications of the patterned thin film of the invention are explained below.

By utilizing the above-mentioned excellent properties and features, e.g. heat resistance, chemical resistance, mechanical properties, electric insulation property and very thin film thickness, the patterned thin films of the present invention can be used in various fields of art such as electronics, energy conversion and material separation.

Firstly, the patterned thin films of the invention can be used as a resist in the field of fine processing of semiconductors by utilizing the chemical resistance. Further, in view of the feature that the film thickness is uniform and thin and the photosensitivity to X-rays, excimer laser lights, etc., applications as resist for ultra fine processing on the order of submicron or quatermicron are possible.

Also, the patterned films of the invention are applicable to dry etching process by utilizing the heat resistance. Representative dry etching processes are plasma etching, reactive spatter etching, and reactive ion beam etching Many materials such as Si, poly-Si, $SiO_2$, $Si_3N_3$ and Al can be processed by altering the reaction gases such as $CF_4$, $CF_4+O_2$, $CF_4+H_2$, $C_3H_8$, $CCl_4$ and $BCl_3$.

The patterned thin films of the invention can be used in electric and electronic devices by utilizing excellent properties in electric conductivity, photoconductivity, optical properties, insulation property, thermal characteristic and chemical reactivity. Applications of the patterned thin films to electric and electronic devices are explained below.

One of the interesting electric and electronic devices having the thin film of the invention is devices having a metal/insulation film/semiconductor (MIS) structure wherein various semiconductors and metals are combined with insulation films. The MIS structure is the fundamental structure of plane electronic devices and integrated circuits.

FIGS. 1 to 7 are schematic views showing typical embodiments of the MIS devices.

In FIG. 1, the thin film of the present invention is provided as insulation film 2 on semiconductor 3 as a substrate, and metal layer 1 is provided as an electrode on the film 2. By using as the substrate a semiconductor of Group IV of the Periodic Table such as Si or Ge, a semiconductor of Group III-V such as GaAs or GaP, or a semiconductor of Group II-VI such as CdTe, CdS, ZnS, ZnSe or CdHgTe, there are provided, for instance, a photoelectric conversion element such as solar cell, a light emitting, light receiving or light detecting element such as LED (light emitting diode), EL (electroluminescence) or photodiode, and other various transducers such as gas sensor and thermal sensor. As the semiconductor used in the invention, any of single crystalline semiconductors, polycrystalline semiconductors and amorphous semiconductors can be used.

Figure 2:
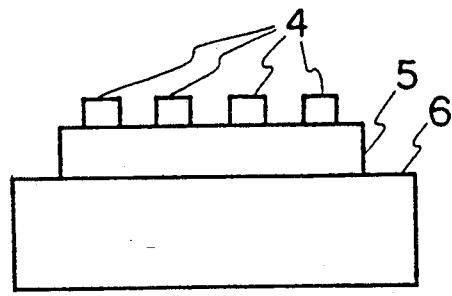

FIG. 2 is a schematic view showing an MIS device wherein 4 is metal electrodes, 5 is an insulation film, and 6 is a semiconductor, having the same structure as the MIS device shown in FIG. 1 except that a plurality of metal electrodes 4 are placed on the insulation film 5. In case of forming two or more elements on the substrate, a plurality of metal electrodes are provided. By utilizing such a structure, charge-transfer devices such as CCD (charge-coupled device) can be prepared, which are interesting applications.

Figure 3:
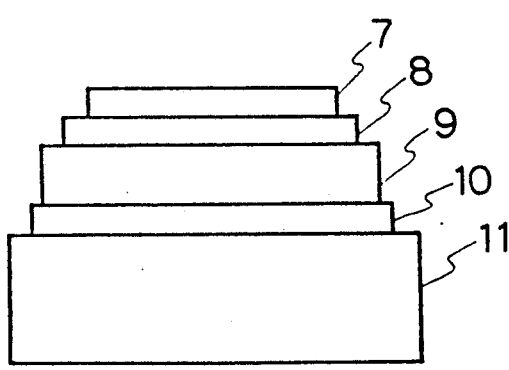

In the MIS device shown in FIG. 3, semiconductor 9 which is, in many cases, in the form of a thin film, is formed on electrode 10 which may be transparent and of course may be patterned, and which is provided on insulation substrate 11. On the semiconductor 9, there is provided an insulation film-carrying electrode composed of insulation thin film 8 of the invention and electrode 7.

Figure 4:
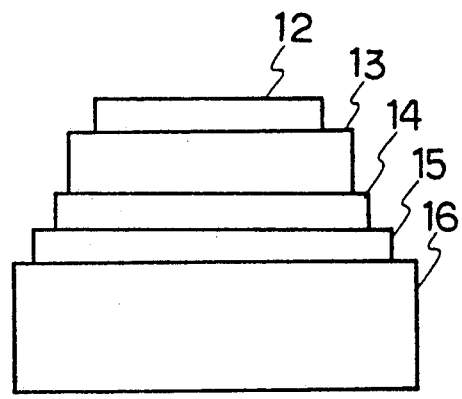

The MIS device shown in FIG. 4 has a similar structure to the device shown in FIG. 3 except that thin film 14 of the invention is placed between metal electrode 15 provided on insulation substrate 16 and thin semiconductor layer 13 on which metal electrode 12 is provided.

The semiconductor thin film can be prepared in various manners adopted usually for preparing semiconductor thin films, e.g. molecular beam epitaxy (MBE), metal organic chemical vapor deposition (MOCVD), atomic layer epitaxy (ALE) deposition, spatter method, spray pyrolysis method, and coating method. In the MIS devices shown in FIGS. 3 and 4, the same semiconductors as used in the MIS devices shown in FIGS. 1 and 2 can be used, and the obtained devices are applicable to the same purposes as those of the devices shown in FIGS. 1 and 2. In the MIS device shown in FIG. 4, it is not desirable that the temperature at which the semiconductor film is formed, is over the heat resistance of the thin film 14 of the invention, since the semiconductor film 13 is formed on the thin film 14 of the invention. The thin films of the ring-closed polymers have a high heat resistance, and it is possible to built-up amorphous silicon on such films, and in future other semiconductors would be applicable to the thin films with development of film forming technique at low temperatures.

Figure 5:
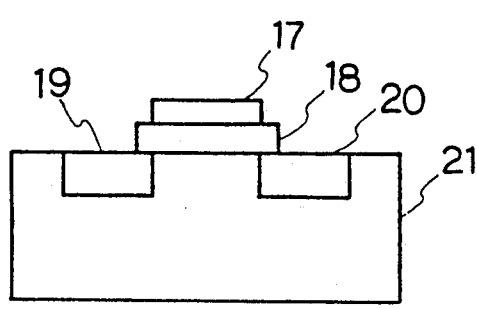
Figure 6:
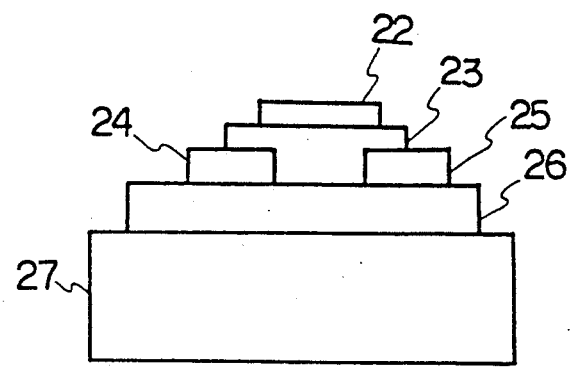

FIGS. 5 and 6 are schematic views showing typical embodiments of MIS device which have a field effect transistor (FET) structure (hereinafter referred to as "MISFET device"), of the type as operated by controlling channel current with gate electrodes, and which are the most important device among MIS devices.

In the MISFET device shown in FIG. 5, a thin film of the invention as insulation film 18 is formed on a semiconductor 21 as a substrate having source 19 and drain 20. A gate electrode 17 is formed on the insulation film 18.

The MISFET device shown in FIG. 6 is different from that shown in FIG. 5 in that semiconductor 26 which is, in many cases, in the form of a thin film, formed on insulation substrate 27, is used instead of the semiconductor substrate 21 shown in FIG. 5. In FIG. 6, shows a gate electrode, 23 shows a thin film of the invention used as an insulation film, 24 shows a source and 25 shows a drain.

The MISFET structure is one of fundamental structure, and various electric and electronic devices can be prepared by utilizing such a structure. For instance, a thin film transistor capable of operating a liquid crystal display can be prepared when assembling on a substrate having a large area, or an integrated circuit (IC) can be obtained by increasing the element number.

In the MISFET devices shown in FIGS. 5 and 6, as interesting applications other than above-mentioned, there are mentioned devices of a structure having no gate electrode. For instance, ion-sensitive FET (ISFET), gas-sensitive FET (Chem FET), immune FET (IMFET), and enzyme FET (ENFET) can be obtained by providing an insulation film, if necessary, with a film capable of responding an ion, gas or active substance. The devices act based on electric field effect caused by acting of the ion, gas or active substance on the surface of the gate insulation film. The advantages of the thin film of the invention as compared with conventional inorganic thin films would be exhibited upon further modifying the thin film with various organic substances. Particularly, in case of thin films of the polymers having long chain alkyl groups, an interaction between the hydrophobic property of the alkyl group and the hydrophobic portion of proteins can be utilized.

Figure 7:
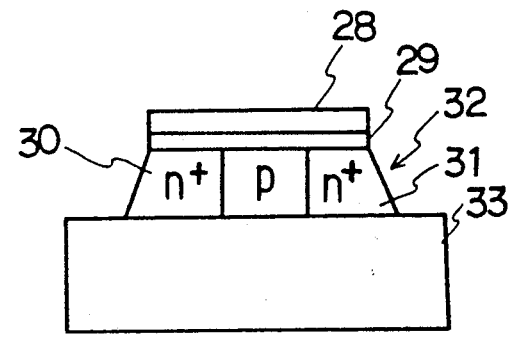

FIG. 7 is a schematic view showing ISFET wherein semiconductor film 32 is formed on a quartz substrate 33 as an insulation substrate, and the thin film of the invention 29 as an insulation film and ion-sensitive film 28 are formed on the semiconductor film 32 in that order. In FIG. 7, 30 shows a source and 31 shows a drain.

One of the advantages of the present invention is that compounds of Groups III-V and II-VI, on which it is usually difficult to form insulation films having good properties by oxidation or the like, can be used as the materials of the semiconductor of the MIS devices. For instance, in case of using GaAs as the semiconductor upon preparation of the devices having the FET structure, devices having a metal-semiconductor FET (MESFET) structure have been prepared from the viewpoint of the above problem. However, by using the thin film of the invention, devices having MIS structure can be obtained, and improvements in the properties of the devices can be expected by utilizing MIS structure.

Also, when MIS integrated circuits are prepared by using GaAs, not only the effect of lowering the driving voltage is produced, but also there can be obtained integrated circuits capable of operating at high speed (HEMT) which utilize large carrier mobility in the GaAs semiconductor.

Secondarily important electric and electronic devices including the thin films of the invention are devices having a metal/insulation film/metal (MIM) structure.

Figure 8:
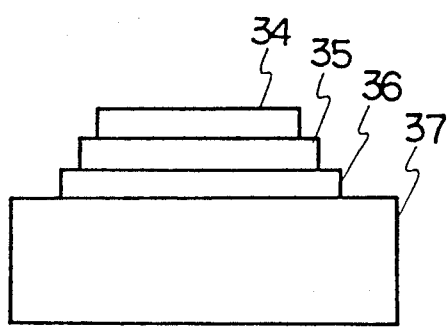
FIGS. 8 to 10 are schematic illustrations of typical devices having a metal/insulation film/metal (MIM) structure.
Figure 9:
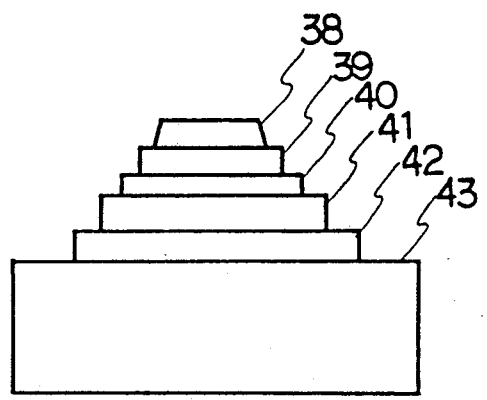
Figure 10:
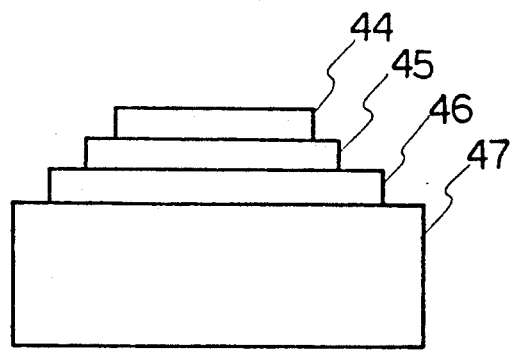

FIGS. 8 to 10 are schematic views showing typical embodiments of the devices having the MIM structure wherein a metal, an insulation film and a metal are formed in order on an insulation substrate or a semiconductor substrate. In FIG. 8, 34 and 36 show metal layers, 35 shows an insulation film and 37 shows an insulation substrate. In FIG. 9, 38, 40 and 42 show metal layers, 39 and 41 show insulation films and 43 shows an insulation substrate. In FIG. 10, 44 and 46 show metal layers, 45 shows an insulation film and 47 shows a semiconductor.

FIG. 8 show the structure of a capacitor. There is provided a moisture sensor in case that the change of capacitance due to moisture is tracked. Also, it is possible to provide a transistor having the MIM structure by utilizing the structure shown in FIG. 8.

When assembled as shown in FIG. 9, a thermionic transistor is obtained.

The MIM device is used as a capacitor of a memory cell in VLSI by forming the capacitor on a semiconductor or a semiconductor device, as shown in FIG. 10. With the MIM structure shown in FIG. 10, it is possible to prepare devices of the type that thermoelectrons are injected into the semiconductor. Further, it is possible to prepare Josephson Junction (JJ) devices by using a superconductor such as Nb instead of the metal.

Figure 11:
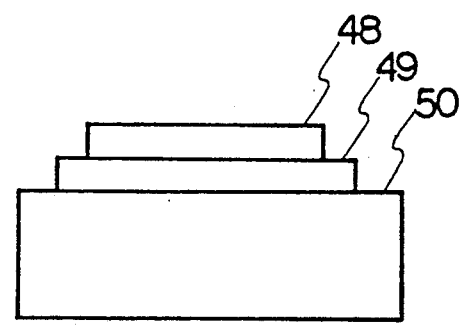
FIGS. 11 to 13 are schematic illustrations of typical devices having an insulation film/metal (IM) structure.
Figure 12:
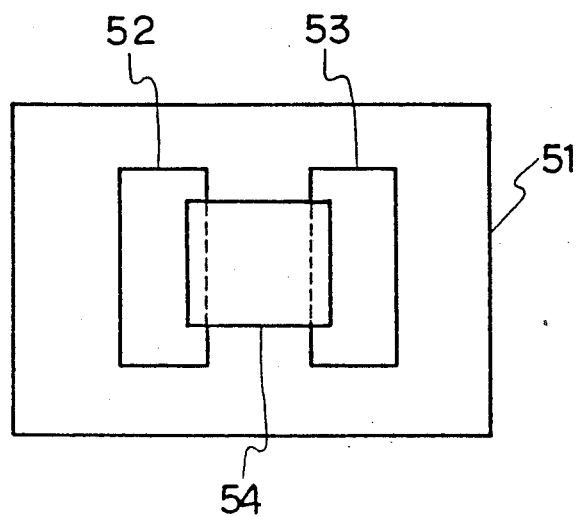
Figure 13:
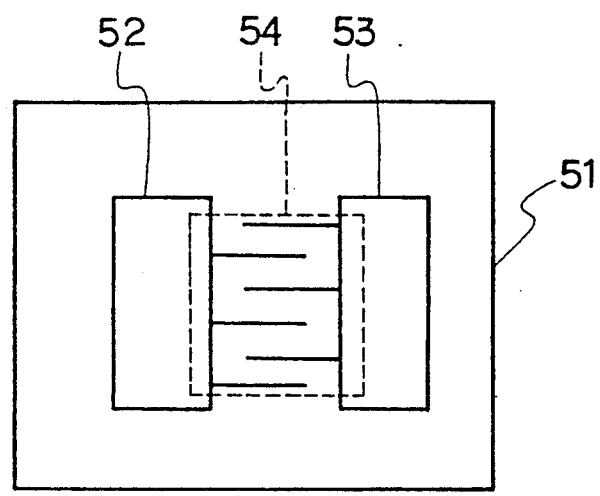

FIG. 11 is a schematic view showing a device having an insulation film/metal (IM) structure wherein thin film 48 of the invention is formed as the insulation film on metal layer 49 formed on insulation substrate 50. The IM device is applied to a liquid crystal orientation film which is obtained by forming the thin film of the present invention on a patterned electrode which is usually a transparent electrode such as ITO. Also, the IM device is used as a moisture sensor or gas senstor, as shown in FIGS. 12 and 13, by forming thin film 54 of the invention on or under two spaced electrodes 52 and 53 provided on or over insulation substrate 51.

Other applications of the electric and electronic devices having the thin film of the invention can be sought in the above-mentioned literatures, particularly in Thin Solid Films, 68, 135 to 171 (1980) P.S. Vincett and G.G. Roberts. Also, with respect to other semiconductor devices and compound semiconductor devices, Fundamentals of Semiconductor Devices by E. S. Yang (Ma-Graw-Hill, 1978), or Kagobutsu Handotai Device [I] or [II], 1984, written and edited by Imai et al, Kogyo Chosakai, can be referred to.

Devices other than the electric and electronic devices are explained below.

There has been attempted to adopt a recording system in which thin films including coloring matter or inorganic thin films such as TeOx are subjected to bit-forming or phase change and the changes are optically read out as 0 or 1. The thin film of the present invention causes a reaction by lights and heat and in particular by laser light which is usually used in optical recording, to change the film thickness, thus resulting in formation of bits. Also, as a result of the above-mentioned reaction, the index of refraction of the thin films is changed. Such a reactivity of the thin films of the invention suggests a utilizability in optical recordation.

In addition, it is also possible to utilize the films of the invention as a cladding material for waveguide and a component for optical circuit. The thin film of the invention has the features that the film thickness can be exactly controlled and the index of refraction can be controlled by changing the compound used in the thin film of the invention. These features are very important factors as the component for the optical circuits.

Further, the thin films of the invention are suitable as protective coating materials in various fields. By utilizing conventional techniques generally used in the field of LB films, such as mixed films or assembled films of functional LB materials and fatty acids, that is, by using the thin films of the present invention instead of the fatty acids, various functionalities can be revealed and the uses utilizing them are considered. For instance, photoelectric devices and biosensors can be fabricated by forming films containing coloring matters or enzymes.

Also, the thin films of the invention are applicable to material separation.

The present invention is more specifically described and explained by means of the following Examples. It is to be understood that the present invention is not limited to the Examples.

EXAMPLE 1

A flask was charged with 2.18 g (0.01 mole) of pyromellitic dianhydride and 5.40 g (0.02 mole) of stearyl alcohol, and they were reacted at about 100° C. for 3 hours in a dry nitrogen stream.

The resulting reaction product was dissolved in 40 ml of hexamethylphosphoramide and cooled to 0° to 5° C. To the solution was added dropwise 2.38 g of thionyl chloride at about 5° C. After the completion of the addition, the solution was maintained at about 5° C. for 1 hour to complete the reaction.

To the reaction mixture was then added dropwise 2 g (0.01 mole) of diaminodiphenyl ether dissolved in 50 ml of dimethylacetamide at a temperature of 0° to 5° C., and after the completion of the addition, the reaction was further continued for about 1 hour. The reaction mixture was poured into 600 ml of distilled water to precipitate the reaction product. The precipitate was filtered and dried under reduced pressure at about 40° C. to give about 9 g of a light yellow powder.

IR absorption analysis, thermal analysis (TGA and DTA), and measurement of molecular weight by gel permeation chromatography (GPC) were made, and it was confirmed that the product was the objective polyimide precursor.

A solution to be spread onto the surface of water for forming a monomolecular film was prepared by dissolving the obtained powder and stearyl alcohol (1:1 by mole) in a mixed solvent of distilled chloroform and dimethylacetamide in a ratio of 8:2 by volume so that the total volume was 25 ml.

The obtained solution was spread onto the surface of bidistilled water to form a monolayer at 20° C., and a built-up film of 21 layers was formed on an aluminum-deposited glass substrate according to the LB method by raising and lowering the substrate through the water surface at a speed of 10 mm/minute, while maintaining the surface pressure of the monolayer on the water surface at about 25 dynes/cm at 20° C.

The built-up film was exposed to a low pressure mercury lamp through a mask for 30 minutes. The exposed film was developed with a mixed solvent of dimethylacetamide and ethanol (1:1 by volume) to give a positive pattern.

The patterned built-up film was then heated at 400° C. for 1 hour. From peaks at 1790 cm$^{-1}$ and 1710 cm$^{-1}$ in FT-ATR-IR analysis, it was confirmed that an $\alpha,\beta$-unsaturated 5-membered cyclic imide was produced.

EXAMPLE 2

A light yellow powder was obtained in the same manner as in Example 1, namely by reacting pyromellitic dianhydride with stearyl alcohol, reacting the resulting reaction product with thionyl chloride, and then reacting the resulting reaction product with diaminodiphenyl ether.

A positive resist material ("HR-1183" made by Fuji-Hunt Electronics) was coated by spin coating in a thickness of about 2 μm on an n-GaAs substrate, and pre-baked at 100° C. for 30 minutes. The coating was exposed to ultraviolet rays through a mask, and developed with a developer (HP.RD 48 developer) to give a resist pattern.

The above powder and stearyl alcohol (1:1 by mole) were dissolved in a mixed solvent of distilled chloroform and dimethylacetamide (8:2 by volume) to give 25 ml of a solution to be spread onto the surface of water for forming a monomolecular film. The obtained solution was spread onto the surface of bidistilled water to form a monolayer at 20° C., and a built-up film of 21 layers was formed on the GaAs substrate having the resist pattern by the vertical dipping method at a deposition speed of 10 mm/minute, while maintaining the surface pressure of the monolayer on the water surface at about 25 dynes/cm at 20° C. The built-up film was then dried overnight.

The substrate was dipped in acetone for 10 seconds to lift off the resist pattern, thereby leaving a patterned LB film on the substrate. It was confirmed that a pattern up to 10 μm line-and-space stripe could be formed.

The patterned LB film was then heated at 400° C. for 1 hour. Production of an α,β-unsaturated 5-membered cyclic imide was confirmed from peaks at 1790 cm$^{-1}$ and 1710 cm$^{-1}$ in FT-ATR-IR analysis.

EXAMPLE 3

A light yellow powder was obtained in the same manner as in Example 1, namely by reacting pyromellitic dianhydride with stearyl alcohol, reacting the resulting product with thionyl chloride, and then reacting the resulting product with diaminodiphenyl ether.

A mask pattern of a polyester tape with an adhesive was formed on a glass substrate so that the mask pattern corresonded to the portion to be removed of a polymer thin film formed after.

The above powder and stearyl alcohol (1:1 by mole) were dissolved in a mixed solvent of distilled chloroform and dimethylacetamide (8:2 by volume) to give 25 ml of a solution to be spread onto the surface of water for forming an LB film. The obtained solution was spread onto the surface of bidistilled water to form a monolayer at 20° C., and a built-up film of 21 layers was formed on the patterned masking tape on the glass substrate by the vertical dipping method at a deposition speed of 10 mm/minute, while maintaining the surface pressure of the monolayer on the water surface at about 25 dynes/cm at 20° C. The patterned masking tape was then removed from the substrate to leave a pattern of the LB film on the substrate. It was confirmed that a line-and space pattern of millimeter level could be formed by this method.

EXAMPLE 4

A built-up film of 31 layers was formed on a silicon wafer in the same manner as in Example 1.

The built-up film was exposed to a low pressure mercury lamp having a main wavelength of 254 nm for 30 minutes through a mask, and developed with ethanol to give a 0.4 μm/1 μm line-and-space pattern. The sensitivity was about 3 J/cm$^2$.

By using the thus obtained resist pattern as a mask, the silicon wafer was subjected to plasma etching with a $CF_4/O_2$ mixed gas. It was confirmed by a Talystep that a depression having a depth of 2 μm was formed in the surface of the silicon wafer.

In addition to the ingredients used in the Examples, other ingredients can be used in the Examples as set forth in the specification to obtain substantially the same results.

What we claim is:

1. A process for preparing a patterned thin film which comprises building up at least one layer of a polymer or a mixture of said polymer and another compound capable of forming a thin film by a Langmuir-Blodgett technique onto a substrate by a Langmuir-Blodgett technique, irradiating patternwise the built-up film with a high energy ray, and developing the irradiated film by applying to the irradiated film a liquid which causes the irradiated portions of the film to dissolve, said polymer having linear recurring units wherein an organic group $R^1$ having at least 2 carbon atoms and a valence of at least 2 is combined alternately with an organic group $R^2$ having at least 2 carbon atoms and a valence of at least 2 through a bivalent group formed by reaction of an acid group A containing a hetero atom and a basic group B containing a hetero atom, and wherein a hydrocarbon-containing group $R^3$ having 10 to 30 carbon atoms is linked by covalent or ionic bonding to said recurring units, the number of group $R^3$ being at least 2 per 10 recurring units.

2. A process for preparing a patterned, heat resistant thin film which comprises building up according to a Langmuir-Blodgett technique at least one layer of a polymer or a mixture of said polymer and another compound capable of forming a thin film by a Langmuir-Blodgett technique on a substrate, irradiating patternwise the built-up film with a higher energy ray, developing the irradiated film by applying to the irradiated film a liquid which causes the irradiated portions of the film to dissolve, and subjecting the remaining built-up film to a reaction to form a 5-membered or 6-membered heterocyclic ring, said polymer having linear recurring units wherein an organic group $R^1$ having at least 2 carbon atoms and a valence of at least 3 is combined alternately with an organic group $R^2$ having at least 2 carbon atoms and a valence of at least 2 through a bivalent group formed by reaction of an acid group A containing a hetero atom and a basic group B containing a hetero atom, and wherein a hydrocarbon-containing group $R^3$ having 10 to 30 carbon atoms is linked by covalent or ionic bonding to said recurring units, the number of groups $R^3$ being at least 2 per 10 recurring units, and said recurring units having a precursor structure capable of forming a 5-membered or 6-membered ring containing a hetero atom.

* * * * *